US011692200B2

(12) United States Patent
Li et al.

(10) Patent No.: US 11,692,200 B2
(45) Date of Patent: Jul. 4, 2023

(54) METHOD FOR IMPROVING RICE YIELD AND/OR RICE BLAST RESISTANCE AND PROTEIN USED THEREOF

(71) Applicant: HUNAN HYBRID RICE RESEARCH CENTER, Changsha (CN)

(72) Inventors: Li Li, Changsha (CN); Yixing Li, Changsha (CN); Dabing Zhang, Changsha (CN); Mudan Qiu, Changsha (CN); Tiankang Wang, Changsha (CN); Shufeng Song, Changsha (CN)

(73) Assignee: HUNAN HYBRID RICE RESEARCH CENTER, Changsha (CN)

( * ) Notice: Subject to any disclaimer, the term of this patent is extended or adjusted under 35 U.S.C. 154(b) by 0 days.

(21) Appl. No.: 17/427,570

(22) PCT Filed: Jan. 21, 2020

(86) PCT No.: PCT/CN2020/073414
§ 371 (c)(1),
(2) Date: Jul. 30, 2021

(87) PCT Pub. No.: WO2020/156367
PCT Pub. Date: Aug. 6, 2020

(65) Prior Publication Data
US 2022/0106605 A1 Apr. 7, 2022

(30) Foreign Application Priority Data

Feb. 2, 2019 (CN) .......................... 201910107261.6
Feb. 2, 2019 (CN) .......................... 201910107277.7

(51) Int. Cl.
*C12N 15/82* (2006.01)
(52) U.S. Cl.
CPC ..... *C12N 15/8261* (2013.01); *C12N 15/8213* (2013.01); *C12N 15/8282* (2013.01)
(58) Field of Classification Search
CPC ............ C12N 15/8261; C12N 15/8213; C12N 15/8282; C12N 15/8262; C12N 15/113; Y02A 40/146; C07K 14/415
See application file for complete search history.

(56) References Cited

U.S. PATENT DOCUMENTS

2006/0041961 A1* 2/2006 Abad ................. C12N 15/8273
800/289
2014/0130203 A1* 5/2014 La Rosa ............. C07K 14/415
536/23.6

OTHER PUBLICATIONS

Chi-Ham, CL, Clark, KL, and AB Bennett; The Intellectual property landscape for gene suppression technologies in plants, Nature Biotechnology, 28, 32-36. (Year: 2010).*
Kirankumar S. Mysore and Muthappa Senthil-Kumar (eds.), Plant Gene Silencing: Methods and Protocols, Methods in Molecular Biology, vol. 1287, Springer Science+Business Media New York 2015 (Year: 2015).*
Mohanta TK et al, Genome editing tools in plants, 2017, Genes, 2017, 399. (Year: 2017).*
"GenBank accession No. BAB90635", GenBank, Feb. 16, 2008; Definition, Features, and Origin parts; URL: https://www.ncbi.nlm.nih.gov/protein/BAB90635.1/.
International Search Report issued in corresponding International Application No. PCT/CN2020/073414 ; dated Apr. 26, 2020; China National Intellectual Administration, Beijing, China, 7 pgs.
Written Opinion issued in corresponding International Application No. PCT/CN2020/073414 ; dated Apr. 26, 2020 China National Intellectual Administration, Beijing, China, 3 pgs.
First Office Action issued in Chinese Application No. 201910107277.7; dated Dec. 13, 2021; 10 pgs.
Sasaki, T., et al.; pentatricopeptide (PPR) repeat-containing protein-like [*Oryza sativa* Japonica Group]; Accession No. BAB90635.1; GenBank Database, Feb. 16, 2008; pp. 1-2.

* cited by examiner

*Primary Examiner* — Anne Kubelik
*Assistant Examiner* — Aleksandar Radosavljevic
(74) *Attorney, Agent, or Firm* — Hauptman Ham, LLP

(57) ABSTRACT

The invention discloses a method for improving rice yield and a protein used thereof. The invention provides a method for cultivating the target rice, comprising the following steps of inhibiting the activity of RAY1 protein in original rice to obtain target rice; compared with the original rice, the target rice shows higher yield and/or larger grain size and/or stronger resistance to rice blast and/or higher plant height and/or longer stem internode length; the RAY1 protein is a protein composed of an amino acid sequence shown as SEQ ID No. 1 in a sequence list. The invention uses CRISPR/Cas9 technology to realize site-directed editing rice RAY1 gene, through knocking out rice RAY1 gene by frameshift mutation, the protein RAY1 is inactivated, and a new generation of rice germplasm with significantly improved yield is obtained.

5 Claims, 7 Drawing Sheets
Specification includes a Sequence Listing.

Figure 3

SEQUENCE LISTING

<160> NUMBER OF SEQ ID NOS: 29

<210> SEQ ID NO 1
<211> LENGTH: 443
<212> TYPE: PRT
<213> ORGANISM: Oryza sativa

<400> SEQUENCE: 1

```
Met Glu Met His Glu Cys Cys Tyr Tyr Gly Gly Ser Ile Gly Gly Asp
1               5                   10                  15

Trp Leu Asn Pro Leu Ala Ala Ile Pro Pro Cys Ser Ser Ser Ser
            20                  25                  30

Ser Ser Trp Ser Ser Gln Leu Leu Leu Ser Asp His Asp Asp Val
        35                  40                  45

Leu Leu His Ser Ala Gly Asp His Gly Gly Ala Val Ala Gly Ile Gly
    50                  55                  60

Gly Ala Cys Met Thr Ala Asp Leu Val Val Arg Asp Glu Glu Met Glu
65                  70                  75                  80

Met Ala Ala Gly Tyr Leu Pro Val Ala Ala Ser Ala Ala Ala Ala Ala
                85                  90                  95

Asp Val Asp His Tyr Met Tyr Gln Gln Phe Gln Leu Glu Pro Asp Gln
            100                 105                 110

Phe Val Ser Thr Leu Pro Ala Val Ala Val Ala Val Ala Ala Thr Ala
        115                 120                 125

Gly Gly Gly Ser His Asp Asp Glu Leu Leu Arg Met Pro Phe Thr Asp
    130                 135                 140

Ile Asp Leu Asp Ala Phe Ala Asp Ala Arg Asp Val Val Val Gly Val
145                 150                 155                 160

Gly Glu Pro Lys Pro Ser Pro Gln His Thr Leu Asp Ala Ala Ile Ala
                165                 170                 175

Leu Pro Ala Val Gly Gly Gly Ala His His Phe Gly Thr Gln Asp
            180                 185                 190

Asp Asp Val Lys Phe Asp Val Thr Lys Gln Arg Asn Asp Ala Ala Leu
        195                 200                 205

Ala Gly Asp Asp Ser Leu Ser Met Val Ile Val Glu Ser Tyr Glu Met
    210                 215                 220

Gly Met Arg Arg His Ala Ala Glu Gln Glu Gln Glu Gln Lys Pro Lys
225                 230                 235                 240

Ile Ile Thr Ser Ala Ala Thr Thr Leu Thr Pro Leu Pro Leu Pro Pro
                245                 250                 255

Pro Pro Pro Pro Pro Arg Val Thr Arg Ser Arg Arg Asp Gly Ser
            260                 265                 270

Ser Ala Ala Thr Ala Gly Gly Lys Thr Arg Leu Asp His Ile Gly Phe
        275                 280                 285

Glu Asp Leu Arg Arg Tyr Phe Tyr Met Pro Ile Thr Lys Ala Ala Arg
    290                 295                 300

Glu Met Asn Val Gly Leu Thr Val Leu Lys Lys Arg Cys Arg Glu Leu
305                 310                 315                 320
```

Gly Val Ala Arg Trp Pro His Arg Lys Met Lys Ser Leu Lys Ser Leu
            325                 330                 335

Ile Leu Asn Val Gln Glu Met Gly Ser Lys Gly Met Ser Ala Ala Ala
            340                 345                 350

Met Arg Arg Glu Leu Glu Ala Leu Glu Asn Cys Cys Ala Leu Met Glu
            355                 360                 365

Arg Asn Pro Ala Val Glu Leu Thr Glu Arg Thr Lys Lys Leu Arg Gln
            370                 375                 380

Ala Cys Phe Lys Glu Asn Tyr Lys Arg Arg Ala Ala Ala Val Asp
385                 390                 395                 400

Val Leu Asp Leu Asp His Cys Phe Ser Phe Ala Ala Gly His Cys His
                405                 410                 415

Arg His His His Gln Gln Leu Ala Leu Pro Pro Pro Ala Ala Ala
            420                 425                 430

Ala Asp His Arg Arg Arg Asp Phe Phe Gly Tyr
            435                 440

<210> SEQ ID NO 2
<211> LENGTH: 1659
<212> TYPE: DNA
<213> ORGANISM: Oryza sativa

<400> SEQUENCE: 2

| | | |
|---|---|---|
| atggagatgc acgagtgctg ctactacggc ggcagcatcg gcggcgactg gctcaaccca | 60 |
| ctcgccgcca tcccgccgcc gtgttcttcc tcttcttctt cgtggtcgtc gcagcttctc | 120 |
| ctcctcaggt cagtgcattt catttcatca tcgctttggt tattttggt tttgtagaat | 180 |
| tcacgagtag gagtgtagta gtacatgaaa ctgacattgt tgttgaatcg tctcgtgtag | 240 |
| tgatcacgat gacgtactct tgcactccgc cggcgatcat ggcggcgcgg tggccggaat | 300 |
| aggcggcgcc tgcatgaccg ccgatctcgt tgtcaggtga acatcatcat ttcttcacct | 360 |
| tctttctttc tttctgcaac tcgatggatt tattacagcc tagaatttga acggttttga | 420 |
| tcatgtcgtc atcagggacg aggagatgga gatggccgcc ggctacctgc cggtggccgc | 480 |
| gtcggccgcc gccgccgccg acgtcgacca ctacatgtac cagcagtttc agctcgagcc | 540 |
| tgatcagttc gtctcgacgt tgcccgcggt ggcggtggcg gtggcggcga cggcgggcgg | 600 |
| cggcagccac gacgacgagc tcctgaggat gcccttcacc gacatcgacc tcgacgcgtt | 660 |
| cgccgacgcg cgcgacgtcg tcgtcggcgt cggcgagccc aagcccagtc cccagcacac | 720 |
| tctcgacgcg gcgatcgcgc tcccggcggt cggcggcggc ggcgccacc acttcggcac | 780 |
| gcaggacgac gacgtcaagt cgacgtgac caagcaacgc aacgacgccg ccctcgccgg | 840 |
| cgacgactcc ctgtccatgg tgatcgtcga gagctacgag atgggcatgc gacgtcacgc | 900 |
| cgccgagcag gagcaggagc agaagccaaa gatcatcaca tcagccgcaa cgacattgac | 960 |
| gcctcttcct cttcctccac cgccgccgcc gccgccgcgc gtgacgagga gccgccgcga | 1020 |
| cggatcatcg gcggcgacgg cgggcgggaa gactcggctg gaccacatcg gattcgagga | 1080 |
| cctgaggcgg tacttctaca tgccaatcac caaggcggcg agggagatga acgtggggct | 1140 |
| gaccgtgctc aagaagcgct gccgcgagct cggcgtcgcc cggtggcctc accggaagat | 1200 |
| gaagagcctc aagtccctca tcctcaacgt ccaggcacgc atcaacctaa ccctagaac | 1260 |
| cttctcgatc agcctcgtct tcgtcttctt cctccagacc aattcagttc ttgctttgct | 1320 |
| tgcattgcac cgtccgtcca tggcgtgcag gagatgggga gcaaggggat gtcggcggcg | 1380 |
| gcgatgcggc gggagctgga ggcgctggag aattgctgcg cgctgatgga gaggaacccg | 1440 |

```
gcggtggagc tgacggagag gaccaagaag ctgaggcagg cgtgcttcaa ggagaattac   1500
aagcggagga gggcggctgc cgtcgacgtg ctcgacctcg accactgctt cagcttcgcc   1560
gccggtcatt gccaccgcca ccaccaccag cagctggctc tgccgccgcc gccagctgcc   1620
gccgccgacc accgtaggag agatttcttc ggctactga                         1659
```

<210> SEQ ID NO 3
<211> LENGTH: 1332
<212> TYPE: DNA
<213> ORGANISM: Oryza sativa

<400> SEQUENCE: 3

```
atggagatgc acgagtgctg ctactacggc ggcagcatcg gcggcgactg gctcaaccca     60
ctcgccgcca tcccgccgcc gtgttcttcc tcttcttctt cgtggtcgtc gcagcttctc    120
ctcctcagtg atcacgatga cgtactcttg cactccgccg gcgatcatgg cggcgcggtg    180
gccggaatag gcgcgcctg catgaccgcc gatctcgttg tcagggacga ggagatggag     240
atggccgccg gctacctgcc ggtggccgcg tcggccgccg ccgccgccga cgtcgaccac    300
tacatgtacc agcagtttca gctcgagcct gatcagttcg tctcgacgtt gcccgcggtg    360
gcggtggcgg tggcggcgac ggcgggcggc ggcagccacg acgacgagct cctgaggatg    420
cccttcaccg acatcgacct cgacgcgttc gccgacgcgc gcgacgtcgt cgtcggcgtc    480
ggcgagccca agcccagtcc ccagcacact ctcgacgcgg cgatcgcgct cccggcggtc    540
ggcggcggcg gcgcccacca cttcggcacg caggacgacg acgtcaagtt cgacgtgacc    600
aagcaacgca acgacgccgc cctcgccggc gacgactccc tgtccatggt gatcgtcgag    660
agctacgaga tgggcatgcg acgtcacgcc gccgagcagg agcaggagca gaagccaaag    720
atcatcacat cagccgcaac gacattgacg cctcttcctc ttcctccacc gccgccgccg    780
ccgccgcgcg tgacgaggag ccgccgcgac ggatcatcgg cggcgacggc gggcgggaag    840
actcggctgg accacatcgg attcgaggac ctgaggcggt acttctacat gccaatcacc    900
aaggcggcga gggagatgaa cgtggggctg accgtgctca agaagcgctg ccgcgagctc    960
ggcgtcgccc ggtggcctca ccggaagatg aagagcctca agtccctcat cctcaacgtc   1020
caggagatgg ggagcaaggg gatgtcggcg gcggcgatgc ggcgggagct ggaggcgctg   1080
gagaattgct gcgcgctgat ggagaggaac ccggcggtgg agctgacgga gaggaccaag   1140
aagctgaggc aggcgtgctt caaggagaat acaagcgga ggagggcggc tgccgtcgac    1200
gtgctcgacc tcgaccactg cttcagcttc gccgccggtc attgccaccg ccaccaccac   1260
cagcagctgg ctctgccgcc gccgccagct gccgccgccg accaccgtag gagagatttc   1320
ttcggctact ga                                                        1332
```

<210> SEQ ID NO 4
<211> LENGTH: 96
<212> TYPE: DNA
<213> ORGANISM: Artificial Sequence
<220> FEATURE:
<223> OTHER INFORMATION: Synthesized

<400> SEQUENCE: 4

```
atcgtcgaga gctacgagat gttttagagc tagaaatagc aagttaaaat aaggctagtc     60
cgttatcaac ttgaaaaagt ggcaccgagt cggtgc                               96
```

<210> SEQ ID NO 5

```
<211> LENGTH: 533
<212> TYPE: DNA
<213> ORGANISM: Artificial Sequence
<220> FEATURE:
<223> OTHER INFORMATION: Synthesized

<400> SEQUENCE: 5
ctcgcactgg aatcggcagc aaaggaagga atctttaaac atacgaacag atcacttaaa      60
gttcttctga agcaacttaa agttatcagg catgcatgga tcttggagga atcagatgtg     120
cagtcaggga ccatagcaca agacaggcgt cttctactgg tgctaccagc aaatgctgga     180
agccgggaac actgggtacg ttggaaacca cgtgtgatgt gaaggagtaa gataaactgt     240
aggagaaaag catttcgtag tgggccatga agcctttcag gacatgtatt gcagtatggg     300
ccggcccatt acgcaattgg acgacaacaa agactagtat tagtaccacc tcggctatcc     360
acatagatca aagctggttt aaaagagttg tgcagatgat ccgtggcatc gtcgagagct     420
acgagatgtt ttagagctag aaatagcaag ttaaaataag gctagtccgt tatcaacttg     480
aaaaagtggc accgagtcgg tgctttttttt caagagcttg gagtggatgg acc           533

<210> SEQ ID NO 6
<211> LENGTH: 20
<212> TYPE: DNA
<213> ORGANISM: Artificial Sequence
<220> FEATURE:
<223> OTHER INFORMATION: Synthesized

<400> SEQUENCE: 6
atggagatgc acgagtgctg                                                  20

<210> SEQ ID NO 7
<211> LENGTH: 20
<212> TYPE: DNA
<213> ORGANISM: Artificial Sequence
<220> FEATURE:
<223> OTHER INFORMATION: Synthesized

<400> SEQUENCE: 7
atggagatgc acgagtgctg                                                  20

<210> SEQ ID NO 8
<211> LENGTH: 19
<212> TYPE: DNA
<213> ORGANISM: Artificial Sequence
<220> FEATURE:
<223> OTHER INFORMATION: Synthesized

<400> SEQUENCE: 8
tcgtcgagag ctacgagat                                                   19

<210> SEQ ID NO 9
<211> LENGTH: 23
<212> TYPE: DNA
<213> ORGANISM: Artificial Sequence
<220> FEATURE:
<223> OTHER INFORMATION: Synthesized

<400> SEQUENCE: 9
ggcatcgtcg agagctacga gat                                              23

<210> SEQ ID NO 10
<211> LENGTH: 23
<212> TYPE: DNA
<213> ORGANISM: Artificial Sequence
```

-continued

```
<220> FEATURE:
<223> OTHER INFORMATION: Synthesized

<400> SEQUENCE: 10
aaacatctcg tagctctcga cga                                          23

<210> SEQ ID NO 11
<211> LENGTH: 38
<212> TYPE: DNA
<213> ORGANISM: Artificial Sequence
<220> FEATURE:
<223> OTHER INFORMATION: Synthesized

<400> SEQUENCE: 11
ttcagaggtc tctctcgcac tggaatcggc agcaaagg                          38

<210> SEQ ID NO 12
<211> LENGTH: 37
<212> TYPE: DNA
<213> ORGANISM: Artificial Sequence
<220> FEATURE:
<223> OTHER INFORMATION: Synthesized

<400> SEQUENCE: 12
agcgtgggtc tcgaccgggt ccatccactc caagctc                           37

<210> SEQ ID NO 13
<211> LENGTH: 23
<212> TYPE: DNA
<213> ORGANISM: Artificial Sequence
<220> FEATURE:
<223> OTHER INFORMATION: Synthesized

<400> SEQUENCE: 13
cccgacatag atgcaataac ttc                                          23

<210> SEQ ID NO 14
<211> LENGTH: 22
<212> TYPE: DNA
<213> ORGANISM: Artificial Sequence
<220> FEATURE:
<223> OTHER INFORMATION: Synthesized

<400> SEQUENCE: 14
gcgcggtgtc atctatgtta ct                                           22

<210> SEQ ID NO 15
<211> LENGTH: 538
<212> TYPE: DNA
<213> ORGANISM: Artificial Sequence
<220> FEATURE:
<221> NAME/KEY: misc_feature
<222> LOCATION: (14)..(17)
<223> OTHER INFORMATION: n is a, c, g, or t
<220> FEATURE:
<221> NAME/KEY: misc_feature
<222> LOCATION: (522)..(525)
<223> OTHER INFORMATION: n is a, c, g, or t
<220> FEATURE:
<223> OTHER INFORMATION: Synthesized

<400> SEQUENCE: 15
ttcagaggtc tctnnnntgg aatcggcagc aaaggaagga atctttaaac atacgaacag   60
atcacttaaa gttcttctga agcaacttaa agttatcagg catgcatgga tcttggagga  120
atcagatgtg cagtcaggga ccatagcaca agacaggcgt cttctactgg tgctaccagc  180
```

| | |
|---|---|
| aaatgctgga agccgggaac actgggtacg ttggaaacca cgtgtgatgt gaaggagtaa | 240 |
| gataaactgt aggagaaaag catttcgtag tgggccatga agcctttcag gacatgtatt | 300 |
| gcagtatggg ccggcccatt acgcaattgg acgacaacaa agactagtat tagtaccacc | 360 |
| tcggctatcc acatagatca aagctggttt aaaagagttg tgcagatgat ccgtggcagt | 420 |
| tttagagcta gaaatagcaa gttaaaataa ggctagtccg ttatcaactt gaaaaagtgg | 480 |
| caccgagtcg gtgcttttt tcaagagctt ggagtggatg gnnnncgaga cccacgct | 538 |

<210> SEQ ID NO 16
<211> LENGTH: 986
<212> TYPE: DNA
<213> ORGANISM: Artificial Sequence
<220> FEATURE:
<223> OTHER INFORMATION: Synthesized

<400> SEQUENCE: 16

| | |
|---|---|
| ggatgtagga gtcgatgcat gcggccgcta gctcgagagg cgcgccgtag tgctcgcact | 60 |
| ggaatcggca gcaaaggaag gaatctttaa acatacgaac agatcactta aagttcttct | 120 |
| gaagcaactt aaagttatca ggcatgcatg gatcttggag gaatcagatg tgcagtcagg | 180 |
| gaccatagca caagacaggc gtcttctact ggtgctacca gcaaatgctg gaagccggga | 240 |
| acactgggta cgttggaaac cacgtgtgat gtgaaggagt aagataaact gtaggagaaa | 300 |
| agcatttcgt agtgggccat gaagcctttc aggacatgta ttgcagtatg ggccggccca | 360 |
| ttacgcaatt ggacgacaac aaagactagt attagtacca cctcggctat ccacatagat | 420 |
| caaagctggt ttaaaagagt tgtgcagatg atccgtggca tcgtcgagag ctacgagatg | 480 |
| ttttagagct agaaatagca agttaaaata ggctagtccg ttatcaact tgaaaaagtg | 540 |
| gcaccgagtc ggtgcttttt ttcaagagct tggagtggat ggaccctgac actggaatcg | 600 |
| gcagcaaagg attttttcct gtagttttcc cacaaccatt ttttaccatc gaatgatag | 660 |
| gataggaaaa atatccaagt gaacagtatt cctataaaat tcccgtaaaa agcctgcaat | 720 |
| ccgaatgagc cctgaagtct gaactagccg gtcacctgta caggctatcg agatgccata | 780 |
| caagagacgt tagtaggaac taggaagacg atggttgatt cgtcaggcga aatcgtcgtc | 840 |
| ctgcagtcgc atctatgggc ctggacggaa taggggaaaa agttggccgg ataggaggga | 900 |
| aaggcccagg tgcttacgtg cgaggtaggc ctgggctctc agcacttcga ttcgttggca | 960 |
| ccggggtagg atgcaataga gagcaa | 986 |

<210> SEQ ID NO 17
<211> LENGTH: 64
<212> TYPE: DNA
<213> ORGANISM: Artificial Sequence
<220> FEATURE:
<223> OTHER INFORMATION: Synthesized

<400> SEQUENCE: 17

| | |
|---|---|
| ggcgcgccgt agtgctcgag agacctctga aggagcgtgg gtctcgcggt atcattggcg | 60 |
| cgcc | 64 |

<210> SEQ ID NO 18
<211> LENGTH: 23
<212> TYPE: DNA
<213> ORGANISM: Artificial Sequence
<220> FEATURE:
<223> OTHER INFORMATION: Synthesized

<400> SEQUENCE: 18

```
gatcgtcgag agctacgaga tgg                                             23

<210> SEQ ID NO 19
<211> LENGTH: 24
<212> TYPE: DNA
<213> ORGANISM: Artificial Sequence
<220> FEATURE:
<223> OTHER INFORMATION: Synthesized

<400> SEQUENCE: 19
gatcgtcgag agctacgatg atgg                                            24

<210> SEQ ID NO 20
<211> LENGTH: 21
<212> TYPE: DNA
<213> ORGANISM: Artificial Sequence
<220> FEATURE:
<223> OTHER INFORMATION: Synthesized

<400> SEQUENCE: 20
gatcgtcgag agctacgatg g                                               21

<210> SEQ ID NO 21
<211> LENGTH: 12
<212> TYPE: DNA
<213> ORGANISM: Artificial Sequence
<220> FEATURE:
<223> OTHER INFORMATION: Synthesized

<400> SEQUENCE: 21
gatcgtcgat gg                                                         12

<210> SEQ ID NO 22
<211> LENGTH: 20
<212> TYPE: DNA
<213> ORGANISM: Artificial Sequence
<220> FEATURE:
<223> OTHER INFORMATION: Synthesized

<400> SEQUENCE: 22
cgtcttcatc acctgcaact                                                 20

<210> SEQ ID NO 23
<211> LENGTH: 22
<212> TYPE: DNA
<213> ORGANISM: Artificial Sequence
<220> FEATURE:
<223> OTHER INFORMATION: Synthesized

<400> SEQUENCE: 23
tgtccataca tgcataaaca cg                                              22

<210> SEQ ID NO 24
<211> LENGTH: 20
<212> TYPE: DNA
<213> ORGANISM: Artificial Sequence
<220> FEATURE:
<223> OTHER INFORMATION: Synthesized

<400> SEQUENCE: 24
ctcatcctcg acggctactt                                                 20

<210> SEQ ID NO 25
<211> LENGTH: 20
<212> TYPE: DNA
```

```
<213> ORGANISM: Artificial Sequence
<220> FEATURE:
<223> OTHER INFORMATION: Synthesized

<400> SEQUENCE: 25
atcaggaagc agcaatacgg                                              20

<210> SEQ ID NO 26
<211> LENGTH: 20
<212> TYPE: DNA
<213> ORGANISM: Artificial Sequence
<220> FEATURE:
<223> OTHER INFORMATION: Synthesized

<400> SEQUENCE: 26
gggtgtggga agcacataca                                              20

<210> SEQ ID NO 27
<211> LENGTH: 20
<212> TYPE: DNA
<213> ORGANISM: Artificial Sequence
<220> FEATURE:
<223> OTHER INFORMATION: Synthesized

<400> SEQUENCE: 27
cctcgagcac atccgacttt                                              20

<210> SEQ ID NO 28
<211> LENGTH: 22
<212> TYPE: DNA
<213> ORGANISM: Artificial Sequence
<220> FEATURE:
<223> OTHER INFORMATION: Synthesized

<400> SEQUENCE: 28
tgctatgtac gtcgccatcc ag                                           22

<210> SEQ ID NO 29
<211> LENGTH: 22
<212> TYPE: DNA
<213> ORGANISM: Artificial Sequence
<220> FEATURE:
<223> OTHER INFORMATION: Synthesized

<400> SEQUENCE: 29
tgctatgtac gtcgccatcc ag                                           22
```

METHOD FOR IMPROVING RICE YIELD AND/OR RICE BLAST RESISTANCE AND PROTEIN USED THEREOF

RELATED APPLICATIONS

The present application is a U.S. National Phase of International Application Number PCT/CN2020/073414 filed Jan. 21, 2020, and claims priority to Chinese Application Numbers CN 201910107277.7, filed Feb. 2, 2019, and CN201910107261.6, filed Feb. 2, 2019.

INCORPORATION BY REFERENCE

The sequence listing provided in the file entitled C6351-045_SQL_Modified.txt, which is an ASCII text file that was created on Jul. 30, 2021, and which comprises 15,520 bytes, is hereby incorporated by reference in its entirety.

TECHNICAL FIELD

The invention relates to the field of biotechnology breeding, in particular to a method for improving rice yield and/or rice blast resistance and a protein used thereof.

BACKGROUND ART

As an important food crop, rice (*Oryza sativa*) provides staple food for more than half of the world's population. To fill the huge grain gap caused by population growth and farmland reduction, scientists put forward the theory of rice super-high-yield breeding in the 1980s, that is, combining ideal plant type with heterosis utilization. Plant type plays an important role in rice yield, quality, resistance, and light use efficiency, including plant height, tiller number, tiller angle, and panicle type, among which panicle type is one of the key factors determining rice yield. Therefore, it is important for shaping rice panicle type and improving rice yield by discovering related genes of rice panicle branch development and clarifying the mechanism of rice panicle branch.

Rice blast is a major rice disease caused by *Magnaporthe oryzae* (asexual generation: Pyricularia *oryzae*) and is common in the world. The loss of rice yield caused by it can reach 11%-30%, in the field with a serious disease, the loss can reach 80%, even no yield, which seriously affects the grain yield and quality. The discovery of rice blast resistance genes can provide new gene resources for breeding rice resistant to rice blast.

SUMMARY OF THE INVENTION

The technical problems to be solved by present invention are about how to improve rice yield and/or rice blast resistance.

To solve the technical problem, the disclosure firstly provides a method for cultivating target rice varieties.

The method for cultivating the target rice varieties provided by the invention comprises the following steps of: inhibiting the activity of RAY1 protein in an original rice variety to obtain a target rice variety; compared with the original rice variety, the target rice shows an increase in yield and/or an increase in grain size and/or an increase in resistance to rice blast and/or an increase in plant height and/or internode elongation; the RAY1 protein is a protein composed of an amino acid sequence shown as SEQ ID No. 1 in a sequence list.

In the above method, inhibiting the activity of the RAY1 protein in the original rice variety can be inhibiting all or part of the activity of the RAY1 protein in the original rice variety.

In the above method, the increase in the yield may be an increase in the yield of a single rice plant; the increase in grain size may be an increase in the length of the grain.

In the above method, the increase in rice yield per plant may be reflected in the increase in the length of rice panicle and/or the increase in the total number of grains per panicle and/or the increase in the number of primary branches.

In the above method, inhibiting activity of the RAY1 protein in the original rice can be achieved by losing the function of a gene encoding the RAY1 protein.

The encoding gene of the RAY1 protein can be 1) or 2) as follows:

1) a DNA molecule shown as SEQ ID No. 2 in the sequence list;
2) a DNA molecule shown as SEQ ID No. 3 in the sequence list.

In the above method, the loss of function of the gene encoding the RAY1 protein can be achieved by any means in the prior art to generate deletion mutation, insertion mutation, or base change mutation in the gene, thereby losing the function of the gene.

In the above method, the loss of function of the gene encoding the RAY1 protein may be a total loss of function or a partial loss of function of the gene encoding the RAY1 protein.

In the above method, in order to loss the function of RAY1 protein encoding gene, methods such as chemical mutagenesis, physical mutagenesis, RNAi, gene site-directed editing, or homologous recombination can be adopted.

Whichever method being adopted, either the whole encoding gene of the RAY1 protein, or each element for regulating and controlling the expression of the encoding gene of the RAY1 protein can be used as a target, so long as the loss of gene function can be achieved. For example, exon 1, exon 2, exon 3, and/or exon 4 of the gene encoding RAY1 may be used as a target.

In the above-mentioned gene site-directed editing, zinc finger nuclease (ZFN) technology, transcription activator-like effector nuclease (TALEN) technology or clustered interspaced short palindromic repeats/CRISPR associated (CRISPR/Cas9 system) technology, as well as other techniques enabling site-directed editing of genomes can be adopted.

In a specific embodiment of the invention, the CRISPR/Cas9 technology is adopted, wherein the target sequence involved is TCGTCGAGAGCTACGAGAT (SEQ ID No.8), and the encoding gene of sgRNA (guide RNA) used is shown as SEQ ID No. 4 in the sequence list.

In further detail, a recombinant vector pYLCRISPR/Cas9-MT-RAY1 capable of expressing a guide RNA and Cas9 is used in the present invention. The recombinant vector pYLCRISPR/Cas9-MT-RAY1 is a recombinant vector obtained by replacing a fragment between two Bsa I enzyme digestion sites of the vector pYLCRISPR/Cas9-MTmono with a DNA fragment containing a specific sgRNA encoding gene and a U3 promoter and keeping other nucleotides of the pYLCRISPR/Cas9-MTmono unchanged, specifically, the DNA molecule shown as SEQ ID No. 5 in the sequence list is used for replacing a fragment between two Bsa I enzyme digestion sites of the vector pYLCRISPR/Cas9-MTmono. The method is applicable to any kind of rice, such as: *Oryza sativa* subsp. *japonica* or *Oryza sativa* subsp. *indica*, provided they contain the above target sequences. An illustrative example of the present invention is *Oryza sativa* L. spp. *japonica*.

To solve the technical problem, the invention also claims the application of substances for inhibiting RAY1 protein activity in any one of the following (1) to (5): (1) increasing the yield of rice; (2) improving the resistance of rice to rice blast; (3) increasing the plant height of rice; (4) increasing the stem internode length of rice; (5) increasing the grain size; the RAY1 protein is a protein composed of an amino acid sequence shown as SEQ ID No. 1 in a sequence list.

In the above application, inhibiting the activity of the RAY1 protein can be inhibiting all or part of the activity of the RAY1 protein.

In the application, increasing the yield of the rice can be increasing the single plant yield of the rice; increasing the single plant yield of the rice can be increasing the panicle length and/or the total grain number per panicle and/or the number of primary branches of the rice; increasing the grain size may be increasing length of the grain.

In the above application, the RAY1 protein inhibiting substance can be any one of the following (1) to (3): (1) specific sgRNA, wherein the target sequence of the specific sgRNA is TCGTCGAGAGCTACGAGAT (SEQ ID No.8); (2) a DNA molecule encoding the specific sgRNA of (1); (3) a vector expressing the specific sgRNA of (1).

In the application, the encoding gene of the specific sgRNA is shown as SEQ ID No. 4 in the sequence list.

In the above application, the vector expressing the specific sgRNA is a recombinant vector pYLCRISPR/Cas9-MT-RAY1. The recombinant vector pYLCRISPR/Cas9-MT-RAY1 is a recombinant vector obtained by replacing a fragment between two Bsa I enzyme digestion sites of the vector pYLCRISPR/Cas9-MTmono with a DNA fragment containing a specific sgRNA encoding gene and a U3 promoter and keeping other nucleotides of the pYLCRISPR/Cas9-MTmono unchanged; specifically, the DNA molecule shown as SEQ ID No. 5 in the sequence list is used for replacing a fragment between two Bsa I enzyme digestion sites of the vector pYLCRISPR/Cas9-MTmono.

In the above application, the rice is *Oryza sativa* subsp. *japonica* or *Oryza sativa* subsp. *indica*. The *Oryza sativa* subsp. *japonica* can be *Oryza sativa* L. spp. *japonica*.

To solve the technical problem, the invention further provides a protein RAY1.

The protein RAY1 provided by the invention is a protein composed of an amino acid sequence shown as SEQ ID No. 1 in a sequence list.

Wherein the protein shown in SEQ ID No. 1 consists of 443 amino acid residues.

To solve the technical problem, the invention also provides a gene encoding the protein RAY1.

The gene encoding the protein RAY1 provided by the invention comprises the following 1) or 2):

1) a DNA molecule shown as SEQ ID No. 2 in the sequence list;
2) a coding region being a DNA molecule shown as SEQ ID No. 3 in the sequence list.

Wherein SEQ ID No. 3 in the sequence list consists of 1332 nucleotides and encodes the protein shown as SEQ ID No. 1 in the sequence list.

To solve the technical problem, the invention also provides a specific sgRNA, wherein the target sequence in the rice genome is as follows: TCGTCGAGAGCTACGAGAT (SEQ ID No.8).

To solve the technical problem, the invention also provides a recombinant plasmid, which comprises an encoding gene of Cas9 protein, an encoding gene of sgRNA, and a U3 promoter; the target sequence of the sgRNA is as follows: TCGTCGAGAGCTACGAGAT (SEQ ID No.8).

BRIEF DESCRIPTION OF THE DRAWINGS

FIG. 3 illustrates the blast result between the pYLgRNA-U3-RAY1 sequencing sequence and the intermediate vector pYLgRNA-U3 sequence. Query represents SEQ ID No.15, Sbjct represents SEQ ID No.16.

DETAILED DESCRIPTION OF THE INVENTION

The following examples facilitate a better understanding of the invention but do not limit it. The experimental procedures in the following embodiments, if not specified, are conventional. The test materials used in the following embodiments, if not specified, are commercially available.

The expression vector pYLgRNA-U3 is described in the literature "Shi Jiangwei, Li Yixing, Song Shufeng, Qiu Mudan, Deng Yao, Li Li. Targeted Editing of Rice Panicle Development Gene Osa1 Mediated by CRISPR/Cas9 System. *HYBRID RICE*, 2017, 32(3): 74-78.", the public can obtain it from the Hunan Hybrid Rice Research Center. The biological material is only used for repeating the relevant experiments of the present invention and cannot be used for other purposes.

The expression vector pYLCRISPR/Cas9-MTmono is described in the literature "Shi Jiangwei, Li Yixing, Song Shufeng, Qiu Mudan, Deng Yao, Li Li. Targeted Editing of Rice Panicle Development Gene Osal Mediated by CRISPR/Cas9 System. *HYBRID RICE*, 2017, 32(3): 74-78.", the public can obtain it from the Hunan Hybrid Rice Research Center. The biological material is only used for repeating the relevant experiments of the present invention and cannot be used for other purposes.

The rice variety *Oryza sativa* L. spp. *japonica* (NIP) is disclosed in the literature "MP, A Robust CRISPR/Cas9 System for Convenient, High-Efficiency Multiplex Genome Editing in Monocot and Dicot Plants. Mol Plant. 2015 Aug. 3; 8(8):1274-84. Doi: 10.1016/j.molp.2015.04.007. Epub 2015 Apr. 24.", the public can obtain it from the Hunan Hybrid Rice Research Center. The biological material is only used for repeating the relevant experiments of the present invention and cannot be used for other purposes.

The Physiological races ZA18, ZB10, ZB133, ZB20, ZC2, ZC10 and ZG1 of *Magnaporthe oryzae* are disclosed in the literature: "Characterization of molecular identity and pathogenicity of rice blast fungus in Hunan province of China. Plant Disease, 2017, 101(4): 557-561.", the public can obtain it from the Hunan Hybrid Rice Research Center. The biological material is only used for repeating the relevant experiments of the present invention and cannot be used for other purposes.

Example 1. Cloning and Analysis of RAY1 Protein-Encoding Genes

Figure 1:
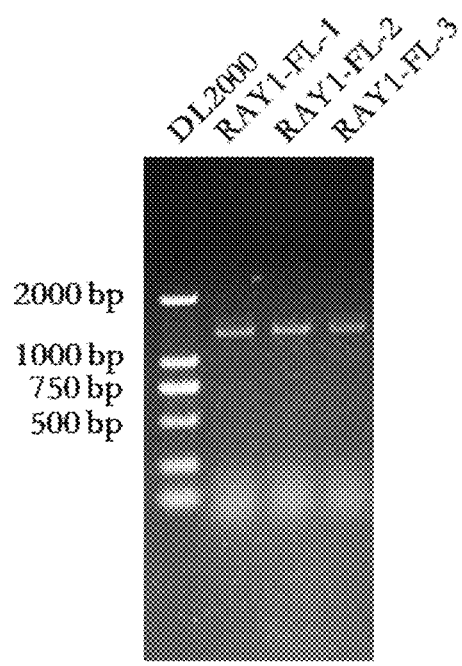
FIG. 1 illustrates the electropherogram of the full-length sequence of PCR amplified RAY1 cDNA.

PCR amplification was performed by using cDNA of *Oryza sativa* L. spp. *japonica* as template, RAY1FL-F (ATGGAGATGCACGAGTGCTG) C SEQ ID No.6) and RAY1FL-R(ATGGAGATGCACGAGTGCTG) (SEQ ID No.7) as primers. The amplification product was a DNA fragment of about 1300 bp in size and the results are shown in FIG. 1. After sequence determination, the DNA fragment was 1332 bp in length and had the nucleotide sequence shown as SEQ ID No. 3 in the sequence list, and was named RAY1. It encodes a protein RAY1 consisting of 443 amino acids, the amino acid sequence of which is shown as SEQ ID No. 1 in the sequence list. The RAY1 gene genomic DNA was 1659 bp in length and contains 4 exons and 3 introns, and the nucleotide sequence of which is shown as SEQ ID No. 2 in a sequence list.

Example 2. Selection of Rice RAY1 Gene Target Site and Construction of Knockout Vector I. Design of Target Sequences In the CDS region of RAY1 gene, the sequence that the 20$^{th}$ bases upstream of NGG was determined as A and the sequence composed of 19 bases downstream of the "A" was selected as the target site (since the transcriptional initiation base of the promoter in the intermediate vector pYLgRNA-U3 is A, which is the same as the 20$^{th}$ base upstream of NGG, therefore the remaining 19 bases are regarded as the target sites to be selected) to obtain the sequence of the target site: TCGTCGAGAGCTACGAGAT (SEQ ID No.8). It locates on the 3$^{rd}$ exon of gDNA of the RAY1 gene, and particularly was a DNA molecule shown in positions from 864 to 882 of SEQ ID No. 2 in the attached sequence list, namely the DNA molecule shown in positions from 653 to 671 of SEQ ID No. 3 in the sequence list.

II. Construction of Recombinant Plasmids

1. Construction of Intermediate Vector pYLgRNA-U3-RAY1

(1) Design and Synthesis of RAY1 Target Site Linker Primer

After the target site sequence was determined, adding GGCA before the 5' of the positive-sense strand and AAAC before the 5' of the antisense strand of the target sequence to obtain the target site linker primer. The target site linker primer sequence is as follows:

```
RAY1-Cas9-F:
                                      (SEQ ID No. 9)
GGCATCGTCGAGAGCTACGAGAT

RAY1-Cas9-R:
                                      (SEQ ID No. 10)
AAACATCTCGTAGCTCTCGACGA
```

(2) Preparation of RAY1 Target Site Linker

Diluting RAY1 target site linker primers RAY1-Cas9-F and RAY1-Cas9-R with ddH$_2$O to obtain mother liquor with the concentration of 10 µM, respectively taking 10 µL to 80 µL of deionized water to obtain a final volume of 100 µL, fully mixing uniformly, carrying out heat shock at 90° C. for 30 s, and moving to room temperature to finish annealing; RAY1 target site linker, labeled RAY1-Cas9, was obtained.

(3) Construction of RAY1 Intermediate Vector

Figure 2:
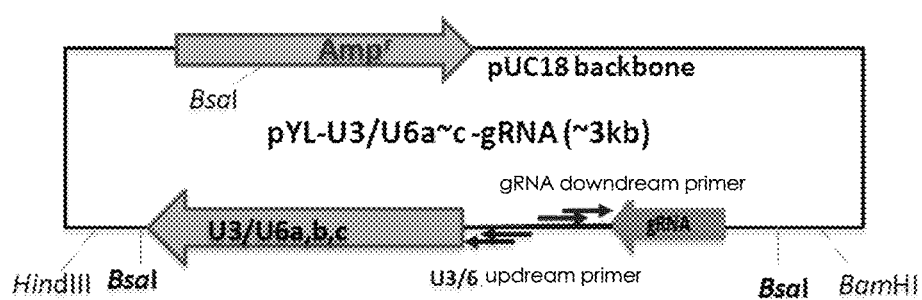
FIG. 2 illustrates the structure map of the intermediate vector pYLgRNA-U3's
Figure 3:
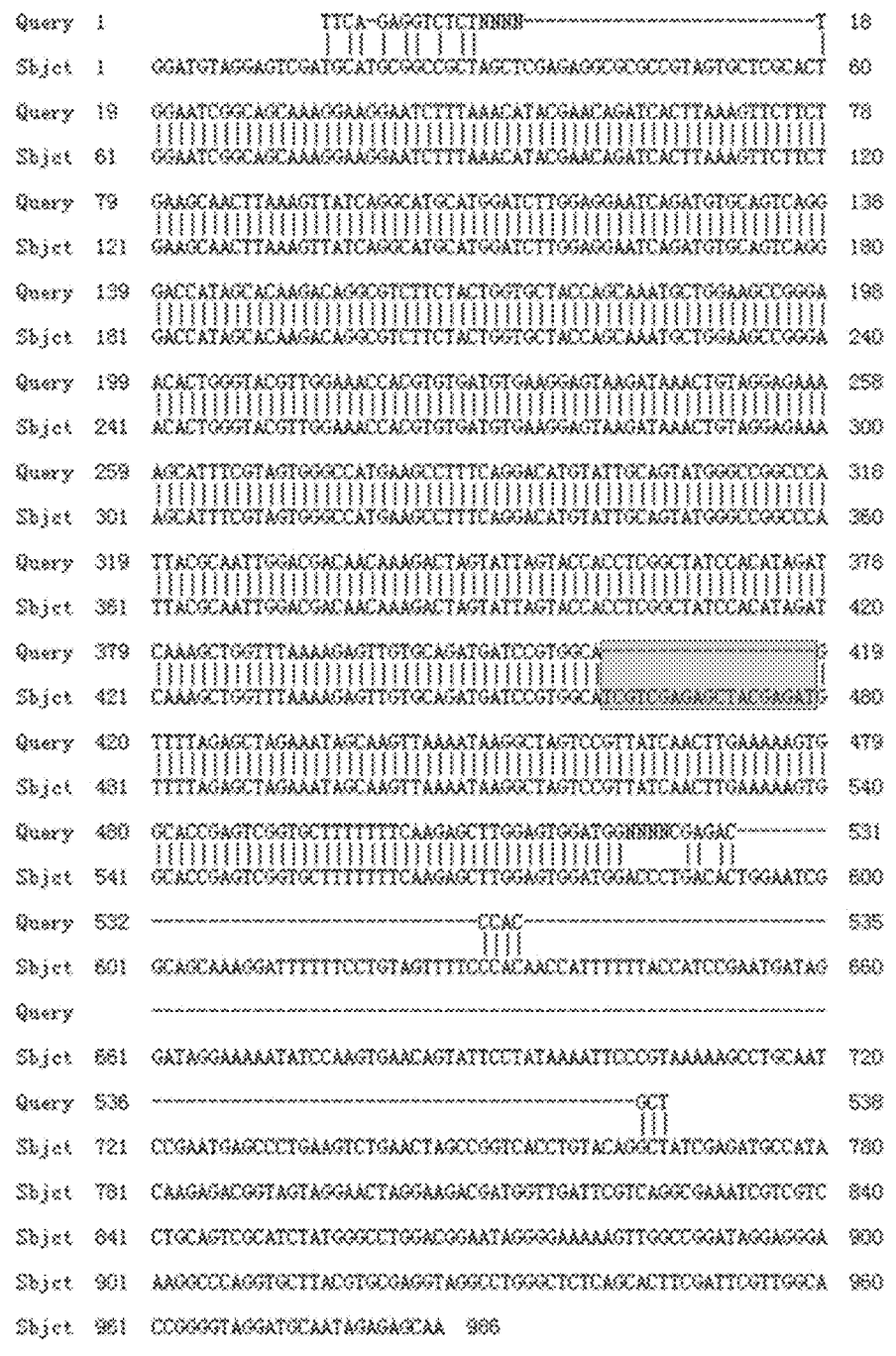

Uniformly mixing 1 µL of pYLgRNA-U3 vector plasmid (shown in FIG. 2), 1 µL of 10×T4 DNA Ligase Buffer, 1 µL target site linker RAY1-Cas9, 1 µL Bsa I restriction enzyme, and 0.5 µL 10×T4 DNA Ligase, and reacting with a PCR instrument. The reaction conditions are as follows: performing 5 cycles at 37° C. for 5 min and at 20° C. for 5 min to obtain the RAY1 intermediate vector. The RAY1 intermediate vector is confirmed by sequencing, and the result shows that: the RAY1 intermediate vector is 19 bases more than the pYLgRNA-U3 vector plasmid, which is the RAY1 target site sequence (shown in FIG. 3 in frame). This indicates that the RAY1 target site sequence has been successfully constructed into the pYLgRNA-U3 vector plasmid, the intermediate vector is named pYLgRNA-U3-RAY1.

2. Construction of Recombinant Vector pYLCRISPR/Cas9-MT-RAY1

(1) Amplification of RAY1 Intermediate Vector Expression Cassette

PCR amplification was performed by using intermediate vector pYLgRNA-U3-RAY1 as template and Uctcg-B1 (TTCAGAGGTCTCTCTCGCACTG-GAATCGGCAGCAAAGG) (SEQ ID No.11) and gRcggt-BL (AGCGTGGGTCTCGACCGGGTCCATCCACTC-CAAGCTC) (SEQ ID No.12) as primers to obtain the amplified product.

Figure 4:
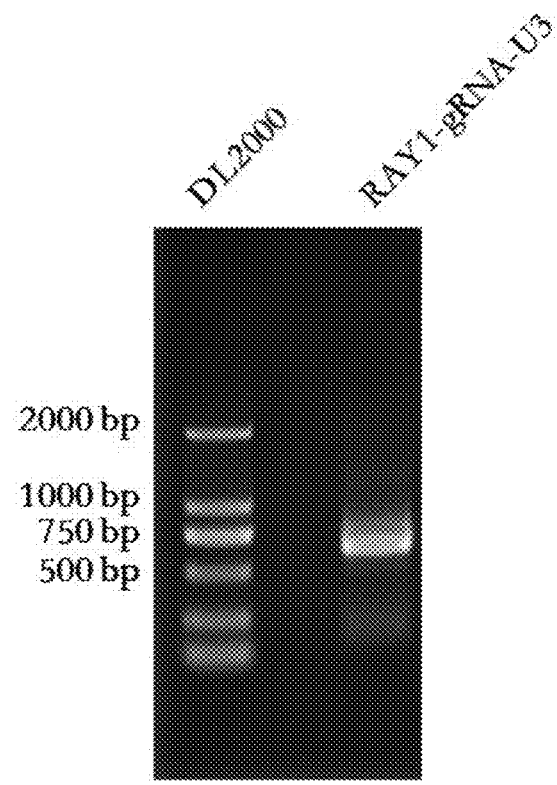
FIG. 4 illustrates the electropherogram for amplification product of the expression cassette of the intermediate vector pYLgRNA-U3-RAY1.

The amplified product was subjected to gel electrophoresis and confirmed to be a DNA molecule of about 550 bp in size (as shown in FIG. 4), and the amplification result was consistent with the expectation. The amplified product was recovered and purified and named RAY1 intermediate vector expression cassette. The expression cassette comprises a sgRNA encoding gene and a U3 promoter, wherein the target sequence of the sgRNA is TCGTCGAGAGCTACGAGAT (SEQ ID No.8), and the sgRNA encoding gene is shown as SEQ ID No. 4 in a sequence list.

(2) Construction and Transformation of RAY1 Site-Directed Editing Final Vector

Figure 5:
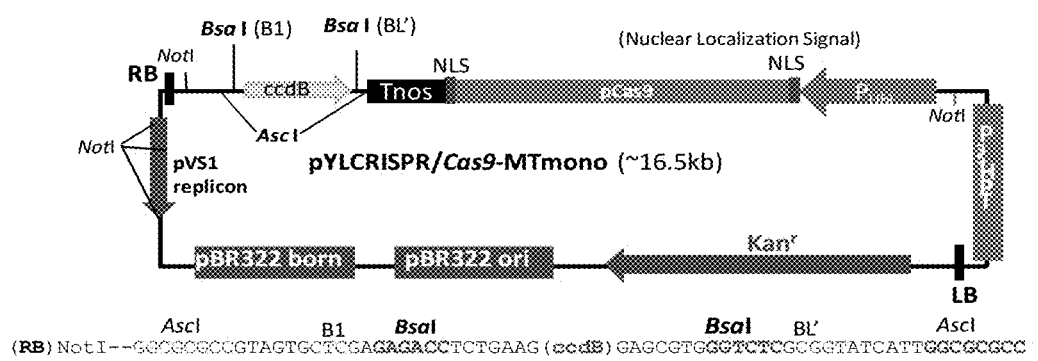
FIG. 5 illustrates the structure map of the genomic editing vector pYLCRISPR/Cas9-MTmono. The nucleotide sequence near the two Bsa I digestion sites is SEQ ID No.17.

The RAY1 gene site-directed editing final vector was obtained by digesting and linking the gene-editing vector pYLCRISPR/Cas9-MTmono (shown in FIG. 5) and RAY1 intermediate vector expression cassette with Bsa I restriction enzyme and T4 DNA Ligase. E. coli was transformed, plated on kanamycin-containing plates and incubated overnight at 37° C.

(3) Detection of Recombinant Vector pYLCRISPR/Cas9-MT-RAY1

Figure 6:
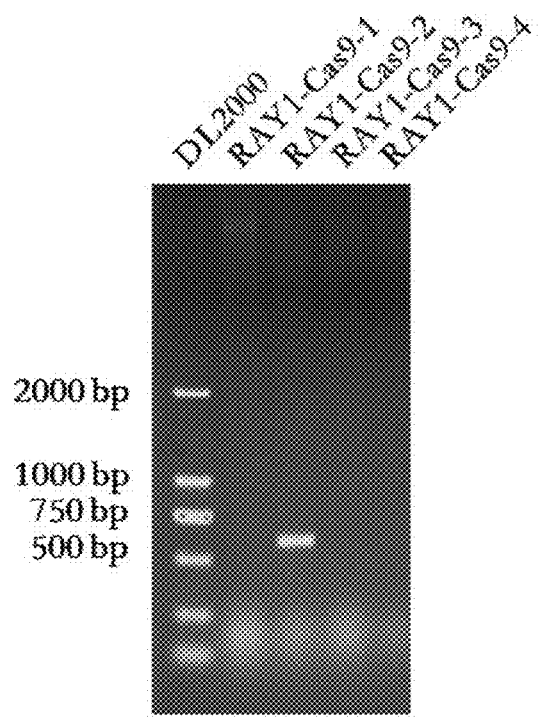
FIG. 6 illustrates the electropherogram of PCR detection of *E. coli.* monoclonal colonies transformed by the recombinant vector pYLCRISPR/Cas9-MT-RAY1

Randomly picking up four monoclonal colonies which are cultured overnight in step (2) and named RAY1-cas9-1, RAY1-cas9-2, RAY1-cas9-3, and RAY1-cas9-4 respectively, and carrying out PCR detection on the four monoclonal colonies by using pYLCRISPR/Cas9-MT vector detection primers SP1 (CCCGACATAGATGCAATAACTTC) (SEQ ID No.13) and SP2 (GCGCGGTGTCATCTATGTTACT) (SEQ ID No.14). The PCR amplified product was subjected to gel electrophoresis, and the electrophoresis results (shown in FIG. 6) showed that the RAY1-cas9-2 monoclonal colony could amplify a band of 550 bp in size, which was consistent with the expectation.

The plasmid DNA of RAY1-cas9-2 monoclonal was extracted and sequenced. The sequencing results show that: the DNA fragment shown in SEQ ID No. 5 in the sequence list successfully replaces the DNA fragment between the two Bsa I digestion sites on the gene editing vector pYLCRISPR/Cas9-Mtmon. This indicated that the expression cassette containing U3 promoter and sgRNA encoding gene was successfully constructed into pYLCRISPR/Cas9-MT-mono, i.e. RAY1 genome site-directed editing vector was successfully constructed to obtain the recombinant vector pYLCRISPR/Cas9-MT-RAY1.

Example 3. Breeding of Target Rice Using Recombinant Plasmids

I. The Recombinant Vector pYLCRISPR/Cas9-MT-RAY1 was Transformed into Oryza sativa L. spp. japonica Using the method of Agrobacterium tumefaciens-mediated transformation of rice callus, the Oryza sativa L. spp. japonica callus was transformed by pYLCRISPR/Cas9-MT-RAY1, and the positive mutants were screened and identified.

II. Detection of Site-Directed Editing

Figure 7:
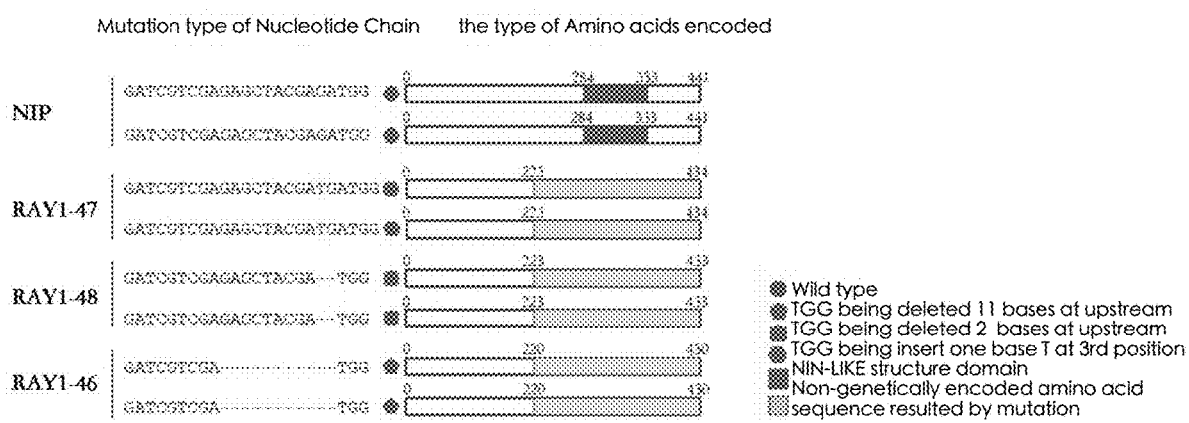
FIG. 7 illustrates the type of RAY1 mutation and the type of amino acids encoded after the mutation. The nucleotide sequence of NIP is SEQ ID No.18, the nucleotide sequence of RAY1-47 is SEQ ID No.19, the nucleotide sequence of RAY1-48 is SEQ ID No.20, the nucleotide sequence of RAY1-46 is SEQ ID No.21.

The positive mutants were detected by PCR and the homozygous mutants of three mutation types were obtained by sequencing and named RAY1-46, RAY1-47, and RAY1-48 respectively. The sequencing results showed (shown in FIG. 7) that the mutant RAY1-46 deleted 11 bases at position 660-670 of RAY1 gene CDS, frameshift appeared at position 220 of RAY1 protein amino acid sequence, and the translation was terminated at position 430; The sequencing results showed that the mutant RAY1-47 has one base T inserted between position 668 and position 669 of RAY1 gene CDS, frameshift appeared at position 223 of RAY1 protein amino acid sequence, and the translation was terminated at position 434; The sequencing results showed that the mutant RAY1-48 deleted 2 bases between position 668 and position 671 of RAY1 gene CDS, frameshift appeared at position 223 of RAY1 protein amino acid sequence, and the translation was terminated at position 433.

III. Phenotype Identification

Normally cultivating the mutant RAY1-46, the mutant RAY1-47, and the mutant RAY1-48, respectively harvesting the $T_1$ generation seeds of the mutant RAY1-46, the mutant RAY1-47, and the mutant RAY1-48, planting the $T_1$ generation seeds, and screening out a $T_1$ generation rice strain which has no exogenous vector and is stable in heredity at the seedling stage. The $T_1$ generation rice lines of the screened mutant RAY1-46, mutant RAY1-47, and mutant RAY1-48 were designated as L-46, L-47, and L-48, respectively. Rice lines L-46, L-47, and L-48 and wild type Oryza sativa L. spp. japonica were planted in plots (control), and 32 rice plants were planted in each plot, and the area of each plot was 1.7 square meters.

Figure 8:
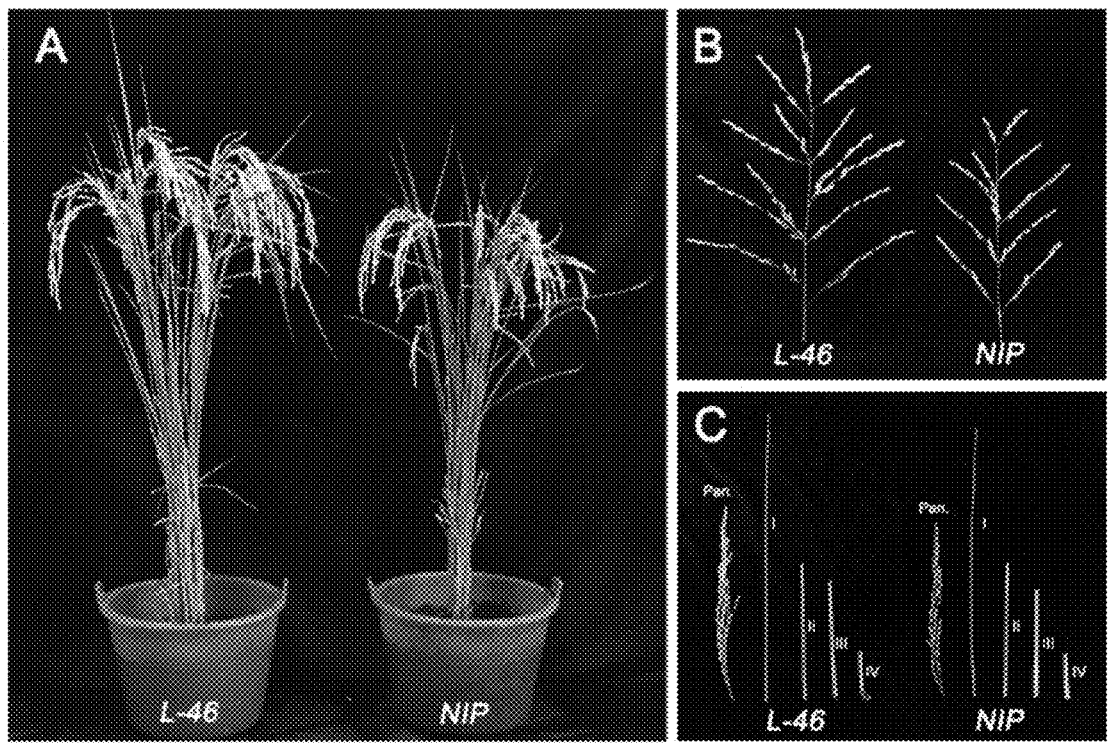
FIG. 8 illustrates the phenotypic comparison between the rice plants of line L-46 and *Oryza sativa* L. spp. *japonica* NIP; wherein, A is plant height and plant type; B is panicle and primary branch; C is panicle length and stem internode length.
Figure 9:
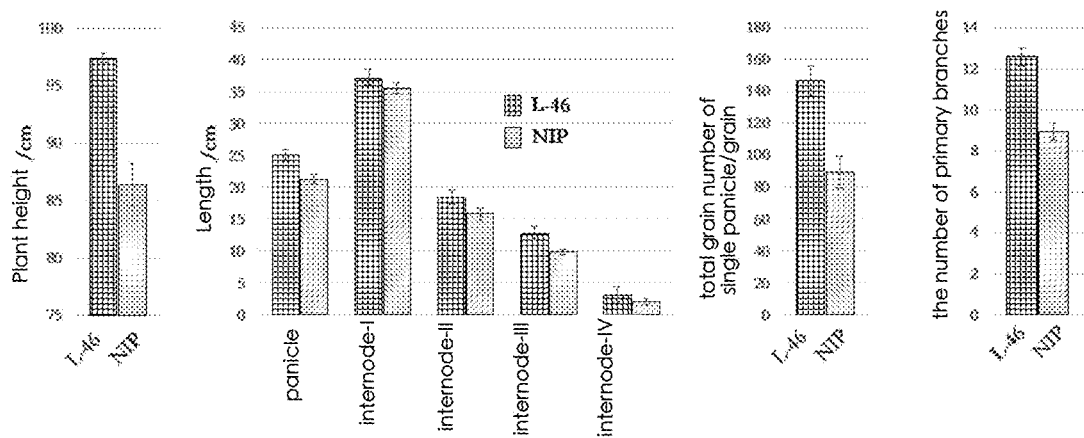
FIG. 9 illustrates the statistical result of agronomic traits of rice plants of line L-46 and *Oryza sativa* L. spp. *japonica* NIP.
Figure 10:
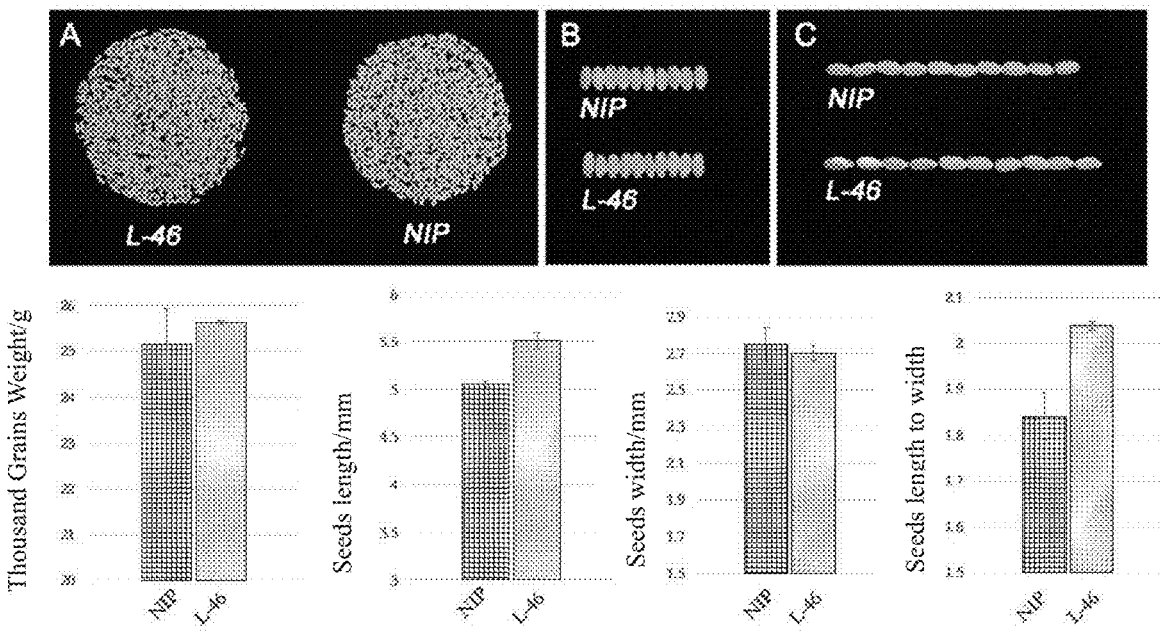
FIG. 10 illustrates the comparison and statistical result of rice traits of the rice plant of line L-46 and the *Oryza sativa* L. spp. *japonica* NIP.

The phenotypes of mutant $T_1$ generation plants and wild type plants were compared. Results as shown in Table 1 and FIGS. 8-10, the stem node elongation of the mutant $T_1$ generation was more significant than that of the wild type plant; the plant height, panicle length, the number of primary branches, and the total number of grains per panicle of the mutant $T_1$ generation plants increased in varying degrees; and the grain length of the mutant $T_1$ generation plants also increased significantly.

TABLE 1

Phenotypic comparison of mutant $T_1$ generation plants and wild type plants

| Phenotype | NIP | L-46 | L-47 | L-48 |
|---|---|---|---|---|
| Plant height (cm) | 86.34 ± 1.85 | 97.40 ± 0.42** | 96.83 ± 0.72** | 96.24 ± 0.67** |
| Panicle length (cm) | 21.27 ± 0.75 | 25.12 ± 0.74** | 25.85 ± 0.64** | 24.89 ± 0.37** |
| Internode I length (cm) | 35.51 ± 0.81 | 37.10 ± 1.44* | 37.51 ± 0.98* | 37.14 ± 1.12* |
| Internode II length (cm) | 15.84 ± 0.97 | 18.44 ± 1.06** | 17.98 ± 1.02** | 18.09 ± 0.89* |
| Internode III length (cm) | 9.83 ± 0.48 | 12.73 ± 1.21* | 11.98 ± 0.89* | 12.64 ± 0.69* |
| Internode IV length (cm) | 2.05 ± 0.50 | 3.09 ± 1.32 | 2.36 ± 1.62 | 2.17 ± 1.06 |
| Total number of grains per panicle | 89.8 ± 10.02 | 146.80 ± 9.34** | 138.67 ± 10.23** | 143.69 ± 10.02** |
| Primary branch number | 8.93 ± 0.44 | 12.60 ± 0.44** | 13.69 ± 0.79** | 12.04 ± 0.68** |
| Grain length (mm) | 5.06 ± 0.03 | 5.51 ± 0.09** | 5.46 ± 0.07** | 5.34 ± 0.11** |
| Grain width (mm) | 2.75 ± 0.09 | 2.7 ± 0.04 | 2.71 ± 0.06 | 2.69 ± 0.06 |
| Grain length-width ratio | 1.84 ± 0.05 | 2.04 ± 0.01** | 2.01 ± 0.04** | 1.98 ± 0.06** |
| 1000-grain weight (g) | 25.15 ± 0.78 | 25.63 ± 0.04 | 25.37 ± 0.34 | 25.69 ± 0.61 |

Note:
*p < 0.05 represents a significant difference from the Oryza Sativa L. spp. japonica, and
**p < 0.01 represents a very significant difference from the Oryza Sativa L. spp. japonica.

Figure 11:
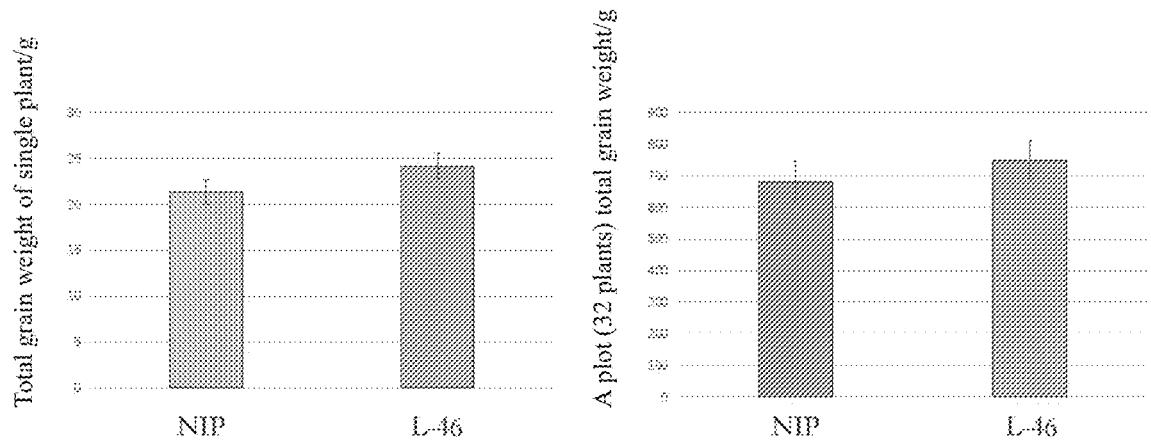
FIG. 11 illustrates the statistical results of a plot total weight and a total weight of single plants of the rice plant of line L-46 and the *Oryza sativa* L. spp. *japonica* NIP.

The yield of mutant $T_1$ generation plants and wild type *Oryza sativa* L. spp. *japonica* rice plants were compared. Results as shown in Table 2 and FIG. 11, compared with wild-type plants, the single plant yield and plot yield of Lines L-46, L-47, and L-48 increased in varying degrees compared with the control.

TABLE 2

Yield Comparison of Mutant T1 generation plants and wild type plants

| Phenotype | NIP | L-46 | L-47 | L-48 |
|---|---|---|---|---|
| Total grain weight per plant (g) | 21.29 ± 1.32 | 24.13 ± 1.36** | 23.89 ± 1.98* | 23.42 ± 1.11* |
| Total grain weight (yield) in the plot (32 plants) (g) | 681.32 ± 62.32 | 749.44 ± 59.35* | 764.48 ± 74.67* | 743.04 ± 55.52* |

Note:
*$p < 0.05$ represents a significant difference from the *Oryza Sativa* L. spp. *japonica*, and
**$p < 0.01$ represents a very significant difference from the *Oryza Sativa* L. spp. *japonica*.

IV. Identifying the Resistance of the Mutant to the Rice Blast

1. Preliminary Detection of Resistance to Rice Blast

The rice blast physiological races ZA18, ZB10, ZB13, ZB20, ZC2, ZC10 and ZG1 were inoculated with rice mutant lines L-46, L-47 and L-48, respectively, and the resistance spectrum of rice blast was determined. At the same time, wild-type *Oryza sativa* L. spp. *japonica* and co39, a type with high susceptibility to rice blast, were used as controls. The specific methods are as follows: different physiological races were prepared into spore suspension with $5\times10^4$ spores/ml by using 5‰ gelatin solution, and the spore suspension was evenly sprayed on the leaf surface of rice seedlings at two-leaf or three-leaf stage with a spray gun. Then the inoculated rice seedlings were cultured in the dark for 24 h, and then transferred to cultivate in the environment with alternating light and dark (12 h of light and 12 h of darkness), in which the ambient temperature was 27° C., the relative humidity is 90%. Each mutant and control was inoculated with 10 rice plants and the experiment was repeated three times. The incidence was investigated one week later (see Table 3 for evaluation criteria). The disease index of mutant and wild type rice plants was calculated according to the incidence.

The rice seedling stage leaf disease index formula is as follows: disease index=Σ (number of diseased plants at each stage×corresponding stage)/(total number of investigated plants×9)×100.

TABLE 3

Criteria for evaluating the incidence of rice plants

| Resistance | Stages | Incidence |
|---|---|---|
| High resistance (hR) | 0 | Disease-free |
| Anti (R) | 1 | Needle size brown spots |
| Anti (R) | 2 | Larger brown spots with a diameter smaller than 1 mm |
| Moderate resistance (mR) | 3 | Gray plaque round to oval with brown margin and diameter in 1 mm~2 mm |
| Moderate resistance (mR) | 4 | Typical spindle-shaped plaque, more than 2 mm in length, usually confined between two veins, with a damaged area of less than 2.0% of the leaf area |
| Moderate resistance (mR) | 5 | Typical spindle-shaped plaque with damage area greater than or equal to 2.0% to less than 10.0% of leaf area |
| Susceptible (S) | 6 | Typical spindle-shaped plaque with damage area greater than or equal to 10.0% to less than 25.0% of leaf area |
| Susceptible (S) | 7 | Typical spindle-shaped plaque with damage area greater than or equal to 25.0% to less than 50.0% of leaf area |
| High susceptible (hS) | 8 | Typical spindle-shaped plaque with damage area greater than or equal to 50.0% to less than 75.0% of leaf area |
| High susceptible (hS) | 9 | Typical spindle-shaped plaque with damage area greater than or equal to 75.0% to less than or equal to 100.0% of leaf area |

Figure 12:
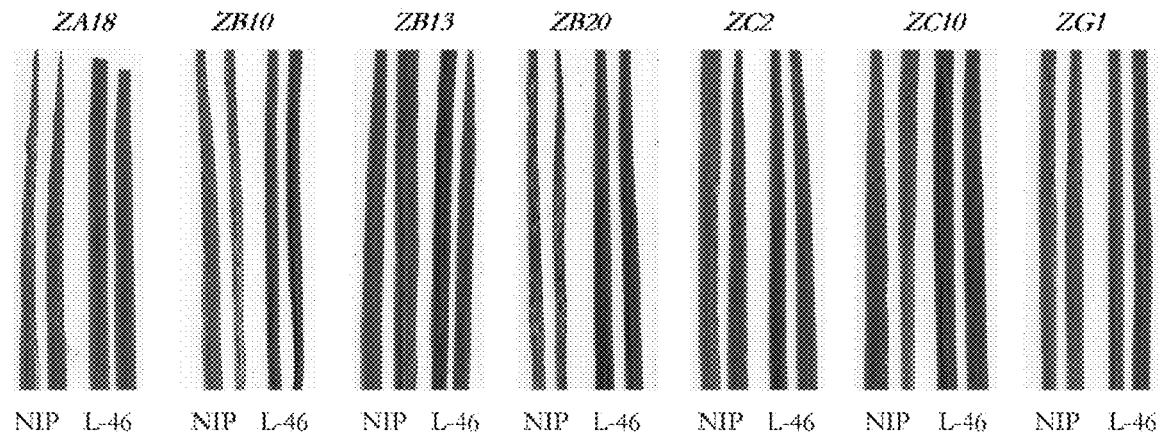
FIG. 12 illustrates an identification result of inoculation of rice blast at the seedling stage of the rice plant of line L-46 and *Oryza sativa* L. spp. *japonica* NIP; wherein, ZA18, ZB10, ZB13, ZB20, ZC2, ZC10, ZG1 are physiological races of rice blast.

As shown in tables 4, 5, and FIG. 12, the disease index of L-46, L-47, and L-48 were much lower than that of wild type *Oryza sativa* L. spp. *japonica* and co39, the wild type *Oryza sativa* L. spp. *japonica* and co39 were not resistant to all races of *Magnaporthe grisea*, while the rice plants of L-46, L-47 and L-48 were resistant to all races of *Magnaporthe grisea*.

TABLE 4

Investigation results on the incidence of mutant T1 generation rice plants and wild-type rice plants

| Physiological race | Rice | | | | |
|---|---|---|---|---|---|
| | co39 | NIP | L-46 | L-47 | L-48 |
| ZA18 | 7 (24 plants); 6 (6 plants) | 7 (16 plants); 6 (6 plants); 0 (8 plants) | 0 (30 plants) | 0 (30 plants) | 0 (30 plants) |
| ZB10 | 7 (22 plants); 6 (8 plants) | 7 (4 plants); 6 (18 plants); 0 (8 plants) | 0 (30 plants) | 2 (3 plants); 0 (27 plants) | 0 (30 plants) |
| ZB13 | 7 (27 plants); 5 (3 plants) | 5 (8 plants); 4 (11 plants); 0 (11 plants) | 0 (30 plants) | 3 (2 plants); 0 (28 plants) | 2 (3 plants); 0 (27 plants) |
| ZB20 | 7 (24 plants); 6 (6 plants) | 7 (15 plants); 6 (7 plants); 5 (3 plants); 0 (5 plants) | 2 (4 plants); 0 (26 plants) | 4 (3 plants); 0 (27 plants) | 2 (3 plants); 0 (27 plants) |
| ZC2 | 7 (22 plants); 6 (8 plants) | 6 (9 plants); 5 (13 plants) 2 (5 plants); 0 (3 plants) | 0 (30 plants) | 0 (30 plants) | 0 (30 plants) |
| ZC10 | 7 (27 plants); 5 (3 plants) | 5 (13 plants); 4 (8 plants); 3 (6 plants); 0 (3 plants) | 0 (30 plants) | 0 (30 plants) | 0 (30 plants) |
| ZG1 | 7 (26 plants); 4 (4 plants) | 6 (13 plants); 5 (8 plants); 4 (4 plants); 0 (5 plants) | 0 (30 plants) | 0 (30 plants) | 0 (30 plants) |

TABLE 5

Statistical table of disease index of mutant T1 generation rice plants and wild type rice plants

| Physiological race | Rice | | | | |
|---|---|---|---|---|---|
| | co39 | NIP | L-46 | L-47 | L-48 |
| ZA18 | 75.6 | 54.8 | 0 | 0 | 0 |
| ZB10 | 74.8 | 50.4 | 0 | 2.2 | 0 |
| ZB13 | 75.6 | 31.1 | 0 | 2.2 | 2.2 |
| ZB20 | 75.6 | 60.0 | 3.0 | 4.4 | 2.2 |
| ZC2 | 74.8 | 47.8 | 0 | 0 | 0 |
| ZC10 | 75.6 | 42.6 | 0 | 0 | 0 |
| ZG1 | 73.3 | 49.6 | 0 | 0 | 0 |

2. Analysis of Expression Characteristics of Rice Blast Resistance-Related Genes OsPR1a, OsPR10, PBZ1 in Strains L-46, L-47 and L-48

The total RNA was extracted from the leaf sheath and leaves of rice varieties *Oryza sativa* L. spp. *japonica*, L-46, L-47, and L-48 respectively, the residual DNA was removed by DNAseDNase I treatment and reverse transcribed into cDNA by OligdT. Using the cDNA as a template, qRT-PCR amplification was performed with primers PR1a-QF/QR (PR1a-QF: CGTCTTCATCACCTGCAACT (SEQ ID No.22) and PR1a-QR: TGTCCATACATGCATAAACACG (SEQ ID No.23)), PR10-QF/QR (PR10-QF: CTCATCCTCGACGGCTACTT (SEQ ID No.24) and PR10-QR: ATCAGGAAGCAGCAATACGG (SEQ ID No.25)), and PBZ1-QF/QR (PBZ1-QF: GGGTGTGG-GAAGCACATACA (SEQ ID No.26) and PBZ1-QR: CCTCGAGCACATCCGACTTT (SEQ ID No.27)) to detect the expression of rice blast resistance related genes OsPR1a, OsPR10 and PBZ1 in *Oryza sativa* L. spp. *japonica*, L-46, L-47, and L-48. ACTIN was used as an internal reference, and the primers used were ACTIN-QF (ACTIN-QF: TGC-TATGTACGTCGCCATCCAG) (SEQ ID No.28) and ACTIN-QR (ACTIN-QR: AATGAGTAAC-CACGCTCCGTCA) (SEQ ID No.29).

Figure 13:
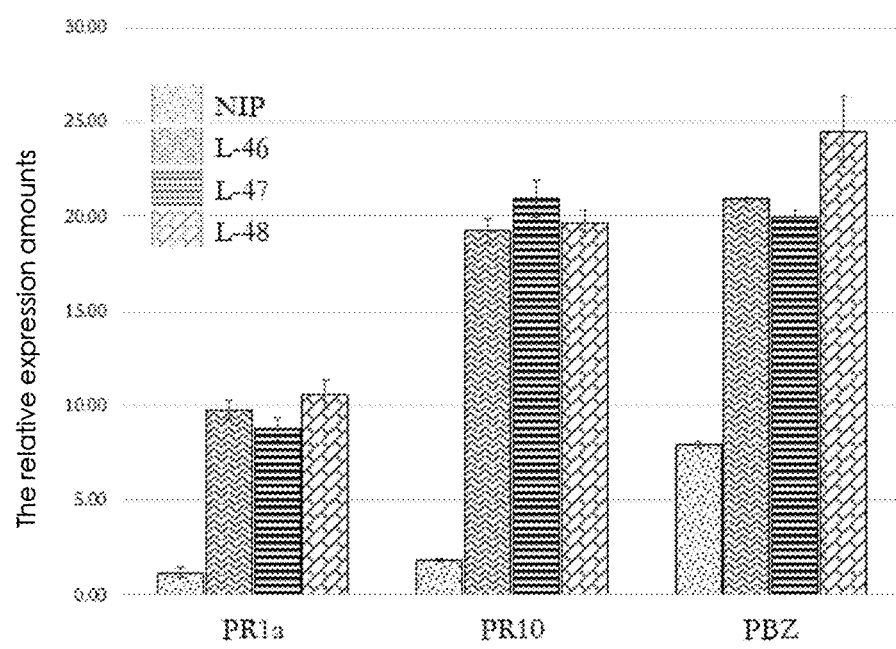
FIG. 13 illustrates the relative expression amounts of the blast resistance-related genes OsPR1a, OsPR10, PBZ1 in the rice plants of lines L-46, L-47, and L-48 and *Oryza sativa* L. spp. *japonica* NIP.

Results as shown in FIG. 13, the expression amount of rice blast resistance related genes OsPR1a, OsPR10, and PBZ1 in L-46, L-47, and L-48 was up-regulated compared with that of rice wild-type variety *Oryza sativa* L. spp. *japonica*. Specifically, compared with *Oryza sativa* L. spp. *japonica*, OsPR1a, OsPR10 and PBZ1 were increased 8.2, 10.6 and 2.6 times in rice mutant line L46, respectively; 7.9, 11.5 and 2.5 times in rice mutant line L47, respectively; and 8.9, 10.8 and 3.0 times in rice mutant line L48, respectively. The results showed that RAY1 gene negatively regulated the expression of rice blast resistance related genes OsPR1a, OsPR10, and PBZ1, thus regulating rice plant resistance to rice blast.

INDUSTRIAL APPLICATIONS

The invention uses CRISPR/Cas9 technology to achieve site-directed editing rice RAY1 gene, through knocking out rice RAY1 gene by frameshift mutation, the protein RAY1 is inactivated, and a new generation of rice germplasm with significantly improved yield and disease resistance are obtained. Compared with the wild type control, the RAY1 site-directed edited lines had higher yield, larger rice grains, longer rice panicles, more panicles, more primary branches, and stronger resistance to rice blast. The invention can be used for improving the yield of rice and the disease resistance to rice blast and provides material for developing new varieties with high yield and disease resistance.

---

The invention claimed is:

1. A method for producing a rice variety, the method comprising:
   transforming a sgRNA expression vector into an original rice variety using a CRISPR/Cas9 method to produce a target rice variety,
   wherein the sgRNA expression vector comprises a target sequence as set forth in SEQ ID NO: 8,
   wherein the transformation causes a loss of function in a gene encoding the RAY1 protein of SEQ ID NO:1;
   wherein said gene has the polynucleotide sequence of SEQ ID NO:2 or SEQ ID NO:3; and
   wherein the target rice variety exhibits an increase in an attribute selected from the group consisting of yield, grain size, resistance to rice blast, height, and internode lengthening relative to the original rice variety.

2. A rice plant or a rice plant part with a loss of function in a gene encoding the RAY1 protein of SEQ ID NO:1.

3. The rice plant or rice plant part according to claim 2, wherein the gene encoding the RAY1 protein is:
   1) the DNA molecule of SEQ ID NO: 2; or
   2) the DNA molecule of SEQ ID NO: 3.

4. The plant or plant part according to claim 2, wherein the rice plant part comprises a plant cell, a plant tissue or plant organs.

5. The plant or plant part according to claim 4, wherein the plant organs comprise seed, leaf, flower, fruit, stem, or root.

* * * * *